United States Patent
Itoh et al.

(10) Patent No.: US 11,331,082 B2
(45) Date of Patent: May 17, 2022

(54) CONTROL DEVICE, IMAGE DIAGNOSIS APPARATUS, METHOD FOR PROCESSING OF CONTROL DEVICE, AND PROGRAM

(71) Applicant: TERUMO KABUSHIKI KAISHA, Tokyo (JP)

(72) Inventors: Ema Itoh, Hadano (JP); Isao Mori, Chofu (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 243 days.

(21) Appl. No.: 16/369,513

(22) Filed: Mar. 29, 2019

(65) Prior Publication Data

US 2019/0223840 A1 Jul. 25, 2019

Related U.S. Application Data

(63) Continuation of application No. PCT/JP2017/033105, filed on Sep. 13, 2017.

(30) Foreign Application Priority Data

Sep. 29, 2016 (JP) .............................. JP2016-192065

(51) Int. Cl.
*A61B 8/00* (2006.01)
*A61B 8/12* (2006.01)
(Continued)

(52) U.S. Cl.
CPC .................. *A61B 8/54* (2013.01); *A61B 1/00* (2013.01); *A61B 1/0125* (2013.01); *A61B 5/0066* (2013.01); *A61B 8/12* (2013.01)

(58) Field of Classification Search
CPC .... A61B 8/54; A61B 1/00; A61B 8/12; A61B 5/0066; A61B 1/0125; A61B 8/5269;
(Continued)

(56) References Cited

U.S. PATENT DOCUMENTS

| 10,478,156 B2 * | 11/2019 | Itoh ..................... A61B 8/5207 |
| 2014/0142427 A1 | 5/2014 | Petroff |
| 2016/0206290 A1 | 7/2016 | Itoh et al. |

FOREIGN PATENT DOCUMENTS

| JP | 1156752 A | 3/1999 |
| WO | 2015045352 A1 | 4/2015 |
| WO | 2015045353 A1 | 4/2015 |

OTHER PUBLICATIONS

The extended European Search Report dated May 8, 2020, by the European Patent Office in corresponding European Patent Application No. 17855736.9-1122. (7 pages).
(Continued)

*Primary Examiner* — Joel Lamprecht
(74) *Attorney, Agent, or Firm* — Buchanan Ingersoll & Rooney PC

(57) ABSTRACT

A control device is disclosed that includes a processor configured to: receive a signal from an imaging core, the imaging core including an optical transceiver and an ultrasound transceiver; determine whether the imaging core is in a state where the ultrasound transceiver can properly execute transmission and reception, based on at least one of the signal from the optical transceiver and the signal from the ultrasound transceiver which are received from the imaging; and control execution of an optical path length adjustment for imaging with the optical transceiver when the ultrasound transceiver can properly execute the transmission and reception.

18 Claims, 12 Drawing Sheets

(51) Int. Cl.
*A61B 5/00* (2006.01)
*A61B 1/012* (2006.01)
*A61B 1/00* (2006.01)

(58) Field of Classification Search
CPC ....... A61B 8/4416; A61B 8/445; A61B 8/085;
A61B 8/4405; A61B 8/0891; A61B
8/0883
See application file for complete search history.

(56) References Cited

OTHER PUBLICATIONS

International Search Report (PCT/ISA/210) dated Oct. 17, 2017, by the Japan Patent Office as the International Searching Authority for International Application No. PCT/JP2017/033105.
Written Opinion (PCT/ISA/237) dated Oct. 17, 2017, by the Japan Patent Office as the International Searching Authority for International Application No. PCT/JP2017/033105.

* cited by examiner

CONTROL DEVICE, IMAGE DIAGNOSIS APPARATUS, METHOD FOR PROCESSING OF CONTROL DEVICE, AND PROGRAM

CROSS-REFERENCES TO RELATED APPLICATIONS

This application is a continuation of International Application No. PCT/JP2017/033105 filed on Sep. 13, 2017, which claims priority to Japanese Application No. 2016-192065 filed on Sep. 29, 2016, the entire content of both of which is incorporated herein by reference.

FIELD OF THE DISCLOSURE

The present disclosure generally relates to a control device, an image diagnosis apparatus, a method for processing of a control device, and a program.

BACKGROUND DISCUSSION

When performing percutaneous treatment of a stenosed site causing a myocardial infarction or the like occurring in a body lumen such as a blood vessel and a vessel, in order to observe characteristics of the stenosed site or to observe condition after the treatment, a diagnostic catheter for acquiring an image of the body lumen by using an inspection wave such as ultrasound or light is used.

In an intra vascular ultrasound (IVUS) diagnosis, an imaging core having an ultrasound transducer at a distal end of an insertion portion is provided in a rotatable manner and inserted into a body-cavity, and then scanning (radial scan) is performed while being rotated through a drive shaft or the like extending from a drive unit on a hand-side.

In optical coherence tomographic (OCT) diagnosis utilizing wavelength sweeping, an optical probe unit having an imaging core inserted in the optical probe unit and equipped with an optical lens and an optical mirror (transceiver) attached at a distal end of an optical fiber is inserted into a blood vessel, measurement light is emitted into the blood vessel from the transceiver at the distal end while rotating the imaging core, and radial scanning in the blood vessel is performed by receiving reflected light from a biological tissue. Generally, a cross-sectional image of a blood vessel is drawn based on interference light generated by causing the received reflected light and reference light to interfere with each other.

In OCT, an image with high resolution is obtained with respect to a vascular lumen surface, but only an image of the relatively shallow tissue from the vascular lumen surface can be obtained. In a case of the IVUS, although IVUS is lower than the OCT in terms of the resolution of the obtained image, conversely, an image of a vascular tissue deeper than the OCT can be obtained. Therefore, recently, an image diagnosis apparatus having an imaging core equipped with a dual sensor combining a function of the IVUS and a function of the OCT (an image diagnosis apparatus including an ultrasound transceiver capable of transmitting and receiving ultrasound, and an optical transceiver capable of transmitting and receiving light) is proposed (see JP-A-11-56752).

However, in a case of a dual sensor, it is necessary to check whether foreign matter such as air bubbles remains before acquiring an IVUS image, and it is also necessary to execute an optical path length adjustment before acquiring an OCT image. At that time, although it is necessary to execute the optical path length adjustment after priming is performed, a user may mistake a procedure and eventually leading to an erroneous diagnosis.

SUMMARY

A technology is disclosed for reducing a burden of prior confirmation by a user and preventing an occurrence of an erroneous diagnosis.

In accordance with an aspect, a control device is disclosed, which includes receiving means for receiving a signal from an imaging core including an optical transceiver and an ultrasound transceiver; determination means for determining whether or not the imaging core is in a state where the ultrasound transceiver is able to properly execute transmission and reception, based on at least one of a signal from the optical transceiver and a signal from the ultrasound transceiver which are received by the receiving means; and control means for performing control so that an optical path length adjustment for imaging with the optical transceiver is executed when the determination means determines that the ultrasound transceiver is able to properly execute the transmission and reception.

In accordance with another aspect, a control device is disclosed comprising: a processor configured to: receive a signal from an imaging core, the imaging core including an optical transceiver and an ultrasound transceiver; determine whether the imaging core is in a state where the ultrasound transceiver is able to properly execute transmission and reception, based on at least one of a signal from the optical transceiver and a signal from the ultrasound transceiver from the signal received from the image core; and control an optical path length adjustment for imaging with the optical transceiver when the ultrasound transceiver is able to properly execute transmission and reception.

In accordance with an aspect, a non-transitory computer readable medium containing a computer program having computer readable code embodied to carry out a method for processing of a control device, the method comprising: receiving a signal from an imaging core including an optical transceiver and an ultrasound transceiver; determining whether the control device is in a state where the ultrasound transceiver is able to properly execute transmission and reception, based on at least one of a signal from the optical transceiver and a signal from the ultrasound transceiver which are received from the signal from the imaging core; and controlling an optical path length adjustment for imaging with the optical transceiver when it is determined that the ultrasound transceiver is able to properly execute the transmission and reception.

In accordance with another aspect, a method is disclosed for processing of a control device, comprising: receiving a signal from an imaging core, the imaging core including an optical transceiver and an ultrasound transceiver; determining whether the control device is in a state where the ultrasound transceiver is able to properly execute transmission and reception, based on at least one of a signal from the optical transceiver and a signal from the ultrasound transceiver which are received from the signal from the imaging core; and controlling an optical path length adjustment for imaging with the optical transceiver when it is determined that the ultrasound transceiver is able to properly execute the transmission and reception In accordance with an exemplary embodiment, a burden of prior confirmation by a user can be reduced, and an occurrence of an erroneous diagnosis can be prevented.

Other features and advantages of the present disclosure will become apparent from the following description with reference to the accompanying drawings. Note that in the accompanying drawings, the same or similar configuration is denoted by the same reference numeral.

BRIEF DESCRIPTION OF THE DRAWINGS

The accompanying drawings are included in the specification, constitute a part of the specification, illustrate embodiments of the present disclosure, and are used to explain the principles of the present disclosure, together with the description.

DETAILED DESCRIPTION

Figure 1:
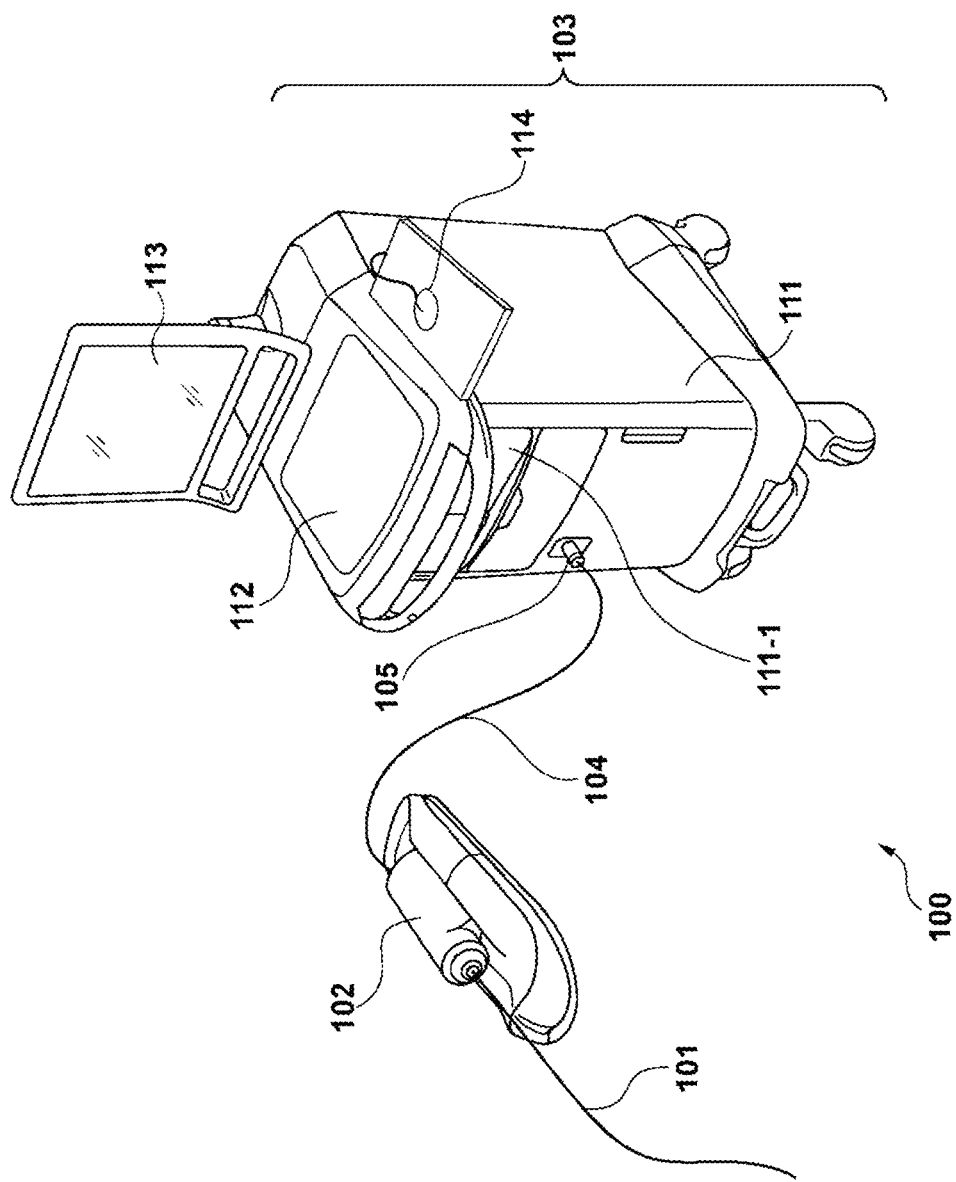
FIG. 1 is a diagram showing an external appearance configuration of an image diagnosis apparatus according to an embodiment of the present disclosure.

Hereinafter, each embodiment of the present disclosure will be described with reference to the drawings. Throughout the drawings, the same reference numerals refer to the same components.

1. External Appearance Configuration of Image Diagnosis Apparatus

An image diagnosis apparatus according to the present embodiment will be described as having an IVUS function and an OCT function. FIG. 1 is a diagram showing an external configuration of an image diagnosis apparatus 100 according to an embodiment of the present disclosure. As shown in FIG. 1, the image diagnosis apparatus 100 includes a probe 101, a scanner and pull-back unit 102, a control device 103, and a display apparatus 113. The scanner and pull-back unit 102 and the control device 103 are connected to each other via a connector 105 by a cable 104 accommodating a signal line and an optical fiber. Note that in the present embodiment, the control device 103 and the display apparatus 113 are described as separate bodies, but the control device 103 may include the display apparatus 113.

In accordance with an exemplary embodiment, the probe 101 is directly inserted into a blood vessel. A catheter accommodating an imaging core that includes an ultrasound transceiver for receiving a reflected wave from the inside of the blood vessel in addition to transmit an ultrasound based on a pulse signal and an optical transceiver for continuously receiving reflected light from the inside of the blood vessel in addition to continuously transmit the transmitted light (measurement light) into the blood vessel, is inserted in the probe 101. The image diagnosis apparatus 100 measures a state inside the blood vessel by using the imaging core.

The probe 101 is detachably attached to the scanner and pull-back unit 102, and by driving a built-in motor, the scanner and pull-back unit 102 defines an axial motion and a rotary direction motion in the blood vessel of the imaging core in the catheter inserted in the probe 101. In addition, the scanner and pull-back unit 102 acquires a reflected wave signal received by the ultrasound transceiver in the imaging core and reflected light received by the optical transceiver, and transmits the signal and the light to the control device 103.

Upon measurement, the control device 103 processes a function for inputting various setting values, or ultrasound data or optical interference data obtained by the measurement, and includes a function for displaying various blood vessel images.

In the control device 103, reference numeral 111 denotes a main control unit. The main control unit 111 generates line data from a reflected wave signal of the ultrasound obtained by the measurement, and generates an ultrasound tomographic image (IVUS image) through an interpolation processing. Furthermore, the main control unit 111 generates interference light data by causing the reflected light from the imaging core and the reference light obtained by separating light from a light source to interfere with each other, and also generates line data based on the interference light data and an optical tomographic image of the blood vessel based on an optical interference through the interpolation processing.

Reference numeral 111-1 denotes a printer and a DVD recorder, which print a processing result in the main control unit 111 and store the processing result as data. Reference numeral 112 denotes an operation panel, and a user inputs various setting values and instructions via the operation panel 112. Reference numeral 113 denotes an LCD monitor as a display apparatus, which displays various cross-sectional images generated by the main control unit 111. Reference numeral 114 denotes a mouse as a pointing device (coordinate input device).

2. Functional Configuration of Image Diagnosis Apparatus (Mainly Control Device)

Figure 2:
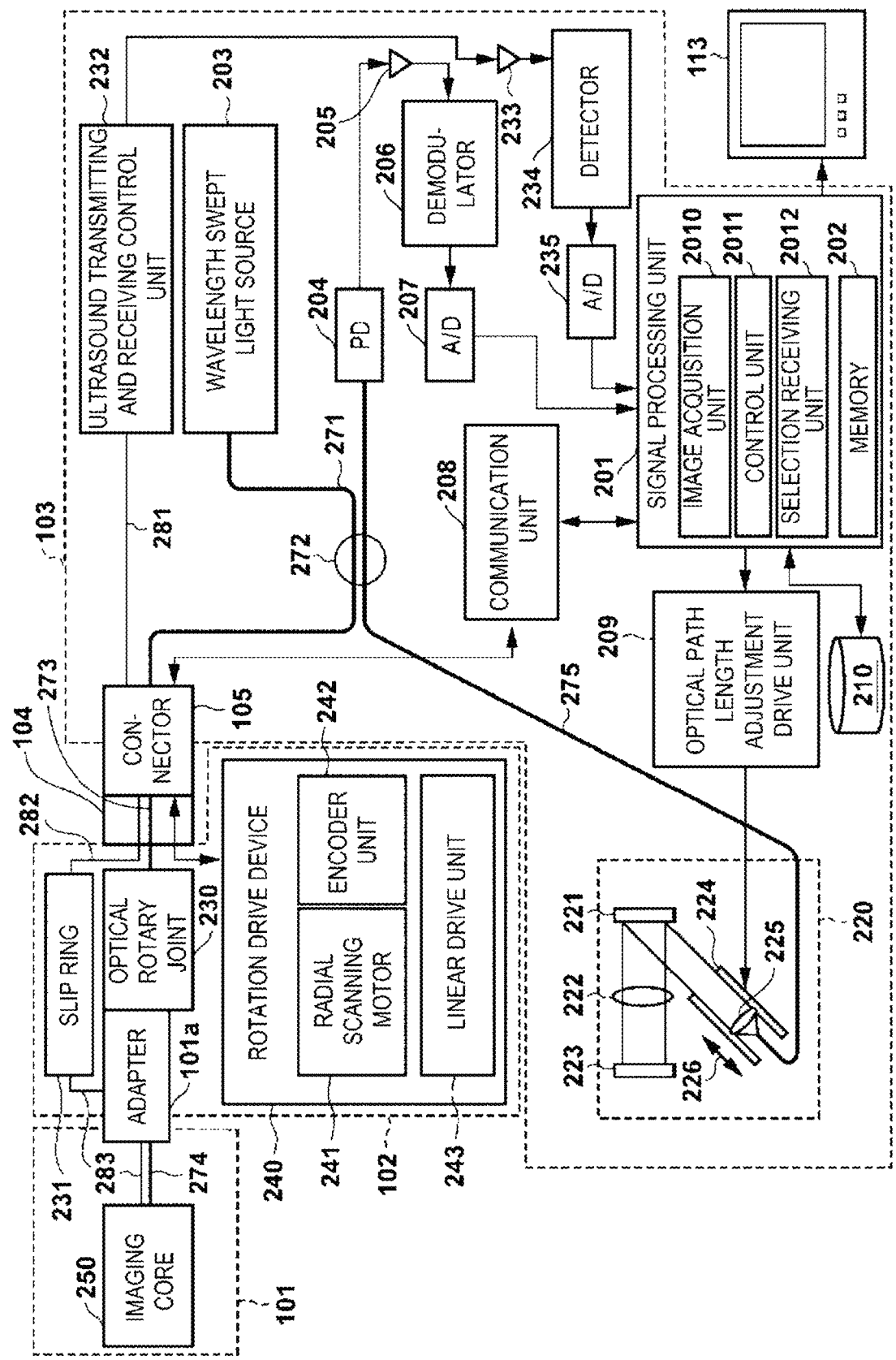
FIG. 2 is a diagram showing a configuration of an image diagnosis apparatus (control device and peripheral devices of the control device) according to the embodiment of the present disclosure.

A functional configuration of the image diagnosis apparatus 100 (mainly the control device 103) will be described. FIG. 2 is a block configuration diagram of the image diagnosis apparatus 100. Hereinafter, the functional configuration for implementing a wavelength sweeping type optical coherent tomographic diagnosis will be described with reference to FIG. 2.

In FIG. 2, reference numeral 201 denotes a signal processing unit, which controls an entire image diagnosis apparatus, and is configured with a microprocessor and number of circuits. Reference numeral 210 denotes a non-volatile storage device typified by a hard disk, and stores various programs or data files to be executed by the signal processing unit 201. Reference numeral 202 denotes a memory (RAM) provided in the signal processing unit 201. Reference numeral 203 denotes a wavelength swept light source, which is a light source that repeatedly generates light having a wavelength that changes within a preset range along a time axis. Reference numeral 2010 denotes an image acquisition unit, which acquires an ultrasound tomographic image (IVUS image) or an optical tomographic image photographed by an imaging core 250 described later. Reference numeral 2011 denotes a control unit, which performs various processes and controls display on the display apparatus 113. Reference numeral 2012 denotes a selection receiving unit, which receives an input from a user via the display apparatus 113, the mouse 114 or the like when the operation panel 112 and the display apparatus 113 have a touch function, and performs various selection processing.

The light output from the wavelength swept light source 203 is incident on one end of a first single mode fiber 271 and is transmitted toward a distal side. The first single mode fiber 271 is optically coupled to a fourth single mode fiber 275 in the middle optical fiber coupler 272.

The light that is incident on the first single mode fiber 271 and is emitted toward the distal side from the optical fiber coupler 272 is guided to a second single mode fiber 273 via a connector 105. The other end of the second single mode fiber 273 is connected to an optical rotary joint 230 in the pull-back unit 102.

In accordance with an exemplary embodiment, the probe 101 has an adapter 101a for connecting with the pull-back unit 102. Then, by connecting the probe 101 to the pull-back unit 102 by using the adapter 101a, the probe 101 is stably held in the pull-back unit 102. Furthermore, an end portion of the third single mode fiber 274 accommodated in the probe 101 in a rotatable manner is connected to the optical rotary joint 230. As a result, the second single mode fiber 273 and the third single mode fiber 274 are optically coupled. An imaging core 250 is provided on the other end of the third single mode fiber 274 (a head part side of the probe 101). The imaging core 250 is equipped with the optical transceiver including a mirror and a lens for emitting light in a direction substantially orthogonal to a rotation axis.

As a result, the light emitted from the wavelength swept light source 203 is guided to the imaging core 250 provided at the end portion of the third single mode fiber 274 via the first single mode fiber 271, the second single mode fiber 273, and the third single mode fiber 274. The optical transceiver of the imaging core 250 emits the light in a direction orthogonal to the axis of the fiber and receives the reflected light. The received reflected light is guided in reverse this time, and returned to the control device 103.

In accordance with an exemplary embodiment, an optical path length adjustment mechanism 220 for finely adjusting an optical path length of the reference light is provided at an opposite end portion of the fourth single mode fiber 275 coupled to the optical fiber coupler 272. The optical path length adjustment mechanism 220 functions as an optical path length change means that changes the optical path length corresponding to a fluctuation in length so as to be able to absorb the fluctuation in length of each probe 101, such as when the probe 101 is exchanged. Therefore, a collimating lens 225 positioned at the end portion of the fourth single mode fiber 275 is provided on a movable one-axis stage 224 as indicated by an arrow 226 which is an optical axis direction of the collimating lens.

Specifically, the one-axis stage 224 functions as an optical path length change means having a variable range of the optical path length that can absorb a fluctuation of the optical path length of the probe 101 when the probe 101 is replaced with a new probe 101, for example, after each operation. Furthermore, the one-axis stage 224 also includes a function as an adjusting means for adjusting an offset. For example, even when the distal end of the probe 101 is not in contact with the surface of the biological tissue, interference with the reflected light from the surface position of the biological tissue can be created by slightly changing the optical path length with the one-axis stage.

In accordance with an exemplary embodiment, the optical path length is finely adjusted by the one-axis stage 224 and light reflected by a mirror 223 via a grating 221 and a lens 222 is guided to the fourth single mode fiber 275. The light is mixed with light obtained from the second single mode fiber 273 side at the optical fiber coupler 272 and received by a photodiode 204 as interference light.

In accordance with an exemplary embodiment, the interference light received by the photodiode 204 in this manner is photoelectrically converted, amplified by an amplifier 205, and then input to a demodulator 206. The demodulator 206 performs demodulation processing for extracting only a signal component of the interfered light, and an output of the demodulator 206 is input to an A/D converter 207 as an interference light signal.

In accordance with an exemplary embodiment, the A/D converter 207 generates single line digital data (interference light data) by sampling the interference light signal, for example, at 90 MHz for 2048 points. In accordance with an exemplary embodiment, the reason why the sampling frequency is set to 90 MHz can be based on the premise that about 90% of the wavelength sweeping cycle (25 μsec) is extracted as digital data of 2048 points when the wavelength sweeping repetition frequency is set to 40 kHz. However, there is no particular limitation to the sampling frequency, which can be set to other sampling frequencies.

The line by line interference light data generated by the A/D converter 207 is input to the signal processing unit 201 and temporarily stored in the memory 202. Then, the signal processing unit 201 performs a frequency decomposition of the interference light data by using fast Fourier transform (FFT) to generate data (line data) in a depth direction, constructs an optical tomographic image at each position in the blood vessel by coordinate-conversion of the data, and outputs the image to the display apparatus 113 at a predetermined frame rate.

The signal processing unit 201 is further connected to an optical path length adjustment drive unit 209 and a communication unit 208. The signal processing unit 201 performs control (optical path length control) of a position of the one-axis stage 224 via the optical path length adjustment drive unit 209.

In accordance with an exemplary embodiment, the communication unit 208 includes several drive circuits and communicates with the pull-back unit 102 under the control of the signal processing unit 201. More specifically, the communication unit 208 is used for supplying a drive signal to a radial scanning motor for rotating the third single mode fiber 274 by the optical rotary joint in the pull-back unit 102, receiving a signal from an encoder unit 242 for detecting a rotational position of the radial motor, and supplying a drive signal to a linear drive unit 243.

Note that the above processing in the signal processing unit 201 is also realized by executing a predetermined program by a computer.

With the above configuration, the probe 101 is positioned at a blood vessel position (coronary artery or the like) of a patient to be diagnosed, and transparent flush liquid is discharged into the blood vessel through a guiding catheter or the like toward the distal end of the probe 101 by a user operation. In accordance with an exemplary embodiment, the transparent flush liquid is to exclude the influence of blood. Then, when the user inputs an instruction to start scanning, the signal processing unit 201 drives the wavelength swept light source 203 to drive the radial scanning motor 241 and the linear drive unit 243 (hereinafter, light irradiation and light receiving processing by driving of the radial scanning motor 241 and the linear drive unit 243 are also referred to as scanning). As a result, wavelength swept light is supplied from the wavelength swept light source 203 to the imaging core 250 through the above-described path. At this time, since the imaging core 250 at the distal position of the probe 101 moves along the rotation axis while rotating, the imaging core 250 performs emission of light to the vascular lumen surface and reception of the reflected light of the imaging core 250 while rotating and while moving along a blood vessel axis.

Figure 3:
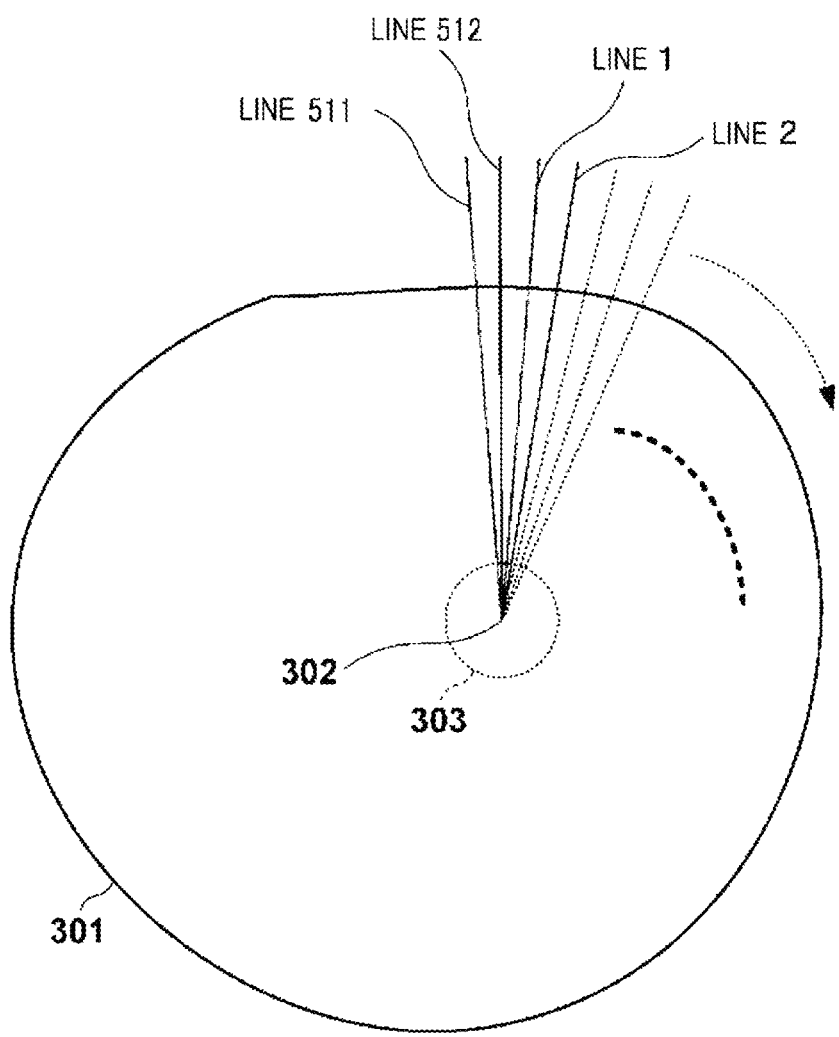
FIG. 3 is a diagram for explaining a cross-sectional image reconstruction processing according to the embodiment of the present disclosure.

Here, processing for generating one optical tomographic image will be briefly described with reference to FIG. 3. FIG. 3 is a diagram for explaining reconstruction processing of a tomographic image of a vascular lumen surface 301 where the imaging core 250 is positioned. While the imaging core 250 makes one rotation (360 degrees), transmission and reception of the measurement light are performed a plurality of times. By transmitting and receiving light one time, single line data in a direction irradiated with the light can be obtained. Therefore, during one rotation, for example, by transmitting and receiving light 512 times, 512 pieces of line data extending radially from a rotation center 302 can be obtained. The 512 pieces of line data are dense in the vicinity of the rotation center position and become sparsely apart from each other as they are away from the rotation center position. Therefore, with respect to pixels in a vacant space of each line, known interpolation processing is performed to generate, and a two-dimensional tomographic image which can be visually perceived by a human is generated.

Figure 4:
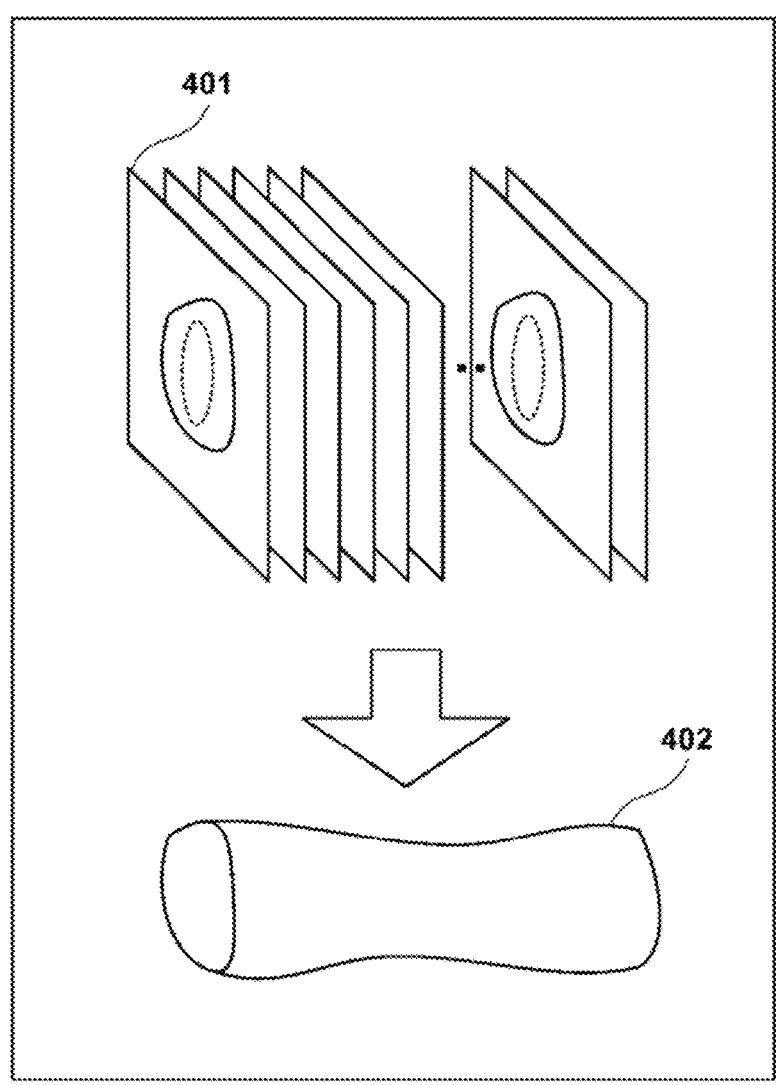
FIG. 4 is a diagram showing an example of three-dimensional model data of a reconstructed blood vessel according to the embodiment of the present disclosure.

Then, as shown in FIG. 4, by connecting generated two-dimensional tomographic images 401 along the blood vessel axis, a three-dimensional blood vessel image 402 can be obtained. Note that a center position of the two-dimensional tomographic image coincides with a rotation center position of the imaging core 250, but not a center position of the blood vessel cross-section. In accordance with an exemplary embodiment, since the light is reflected by a lens surface of the imaging core 250, a surface of the catheter, or the like, several concentric circles occur with respect to the rotation center axis as indicated by reference numeral 303.

Next, a configuration and processing contents relating to an image formation using an ultrasound will be described. Scanning using an ultrasound is performed simultaneously with the above-described optical interference scanning. That is, the ultrasound transceiver accommodated in the imaging core 250 performs an emission of ultrasound and a detection of the reflected wave while performing the scanning, rotating the imaging core 250, and moving in the catheter sheath of the probe 101. Therefore, it is necessary to generate a drive signal for driving the ultrasound transceiver accommodated in the imaging core 250, and receive a detection signal of an ultrasound output by the ultrasound transceiver. An ultrasound transmitting and receiving control unit 232 performs transmission of the drive signal and reception of the detected signal. The ultrasound transmitting and receiving control unit 232 and the imaging core 250 are connected via signal line cables 281, 282, and 283. Since the imaging core 250 rotates, the signal line cables 282 and 283 are electrically connected via a slip ring 231 provided in the pull-back unit 102. Note that in the drawing, the signal line cables 281 to 283 are indicated as being connected by one line, but actually, the signal cables 281 to 283 are a plurality of signal lines, which are accommodated in the slip ring 231 and the control device 103.

The ultrasound transmitting and receiving control unit 232 operates under the control of the signal processing unit 201, drives the ultrasound transceiver accommodated in the imaging core 250, and generates an ultrasound pulse wave. The ultrasound transceiver converts the reflected wave from the vascular tissue into an electric signal, and supplies the electric signal to the ultrasound transmitting and receiving control unit 232. The ultrasound transmitting and receiving control unit 232 outputs the received ultrasound signal to the amplifier 233 and amplifies the ultrasound signal. Thereafter, the amplified ultrasound signal is supplied to the signal processing unit 201 as ultrasound data via a detector 234 and the A/D converter 235, and is temporarily stored in the memory 202. In accordance with an exemplary embodiment, the A/D converter 235 performs a sampling of the ultrasound signal output by the detector 234, for example, at 30.6 MHz for 200 points, and generates single line digital data (ultrasound data). Note that although 30.6 MHz is used here, the sampling of the ultrasound signal output is calculated on the premise that 200 points are sampled for a depth of 5 mm when a sound speed is 1530 m/sec. Therefore, the sampling frequency is not particularly limited to 30.6 MHz and other sampling frequencies can be used.

The signal processing unit 201 generates an ultrasound image at each position in the blood vessel by converting the ultrasound data stored in the memory 202 to grayscale.

3. Processing

Figure 5:
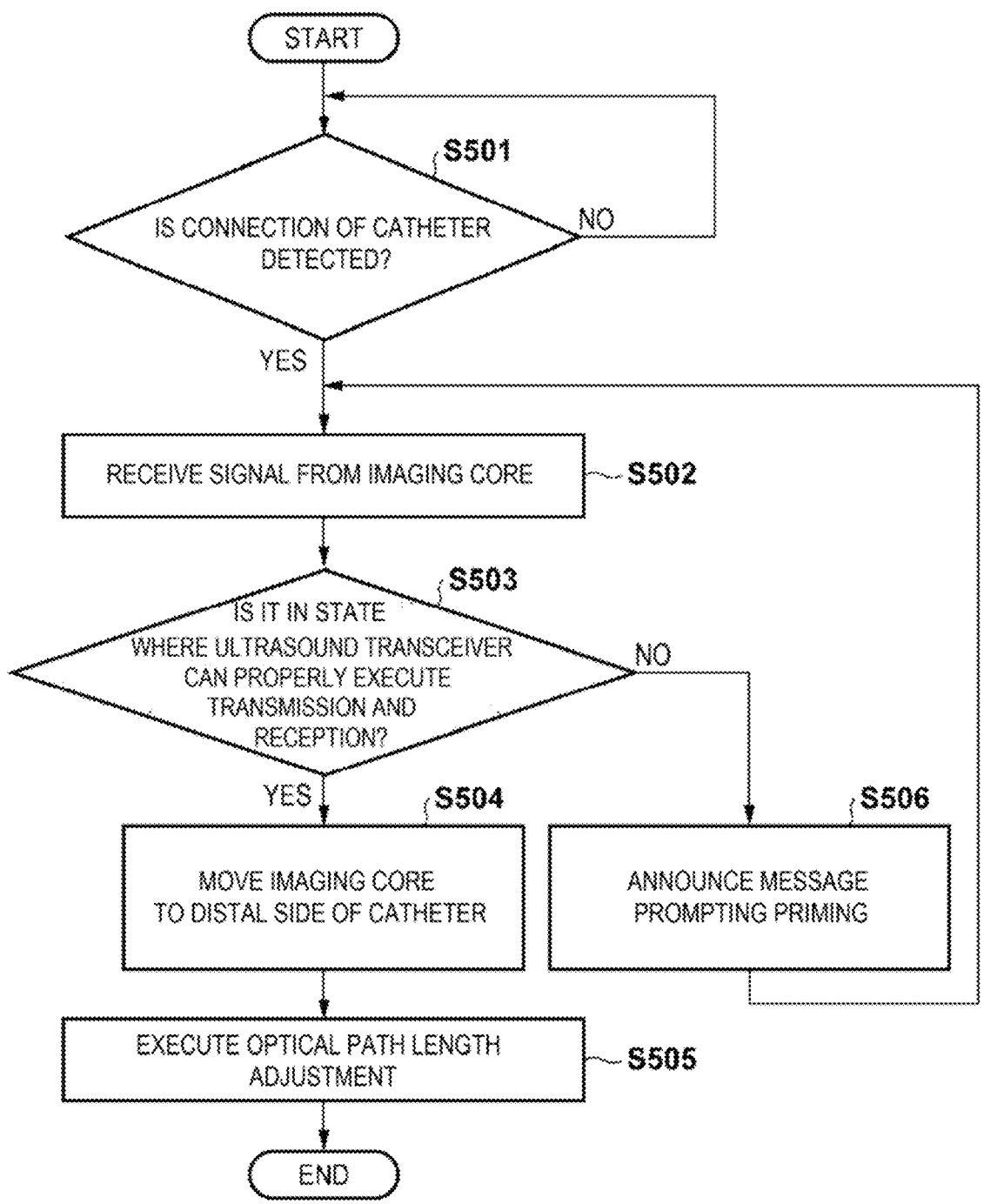
FIG. 5 is a flowchart showing a procedure of processing performed by the control device according to the embodiment of the present disclosure.

Next, with reference to the flowchart of FIG. 5, a procedure of processing performed by the control device 103 according to the embodiment of the present disclosure will be described. The user executes the priming operation before the start of the processing in FIG. 5. In some cases, however, foreign matter such as air bubbles remains. In such cases, the imaging core 250 may not be in a state where the ultrasound transceiver can properly execute transmission and reception of signals, and accordingly, it is necessary to prompt the priming operation again.

In step S501, the control device 103 determines whether or not the catheter accommodating the imaging core 250 is connected to the control device 103. If the connection is detected, the processing proceeds to S502. In accordance with an exemplary embodiment, if the connection is not detected, the processing waits until the connection is detected. In step S502, the control device 103 receives a signal from the imaging core 250. The signal received here is at least one of a signal from the optical transceiver and a signal from the ultrasound transceiver.

In step S503, the control device 103 determines whether or not the imaging core 250 is in a state where the ultrasound transceiver in the imaging core 250 can properly execute the transmission and reception of signals. The state where the ultrasound transceiver can properly execute the transmission and reception of signals may be, for example, a state where no foreign matter such as air bubbles remains in the catheter accommodating the imaging core 250. In the processing in S502 and S503, a determination can be made based on a signal of the ultrasound transceiver, or a determination can be made based on a signal of the optical transceiver, or a determination can be made using signals of both of the transceivers. More details of the processing in S502 and S503 will be described later. If the imaging core 250 is in a state where the transmission and reception can be properly executed, the processing proceeds to S504. In accordance with an exemplary embodiment, if the imaging core 250 is not in a state where the transmission and reception can be properly executed, the processing proceeds to S506.

In step S504, the control device 103 moves the imaging core 250 toward the distal side of the catheter before executing the optical path length adjustment processing described later. In step S505, the control device 103 performs control so as to execute the optical path length adjustment for imaging using the optical transceiver of the imaging core 250. More specifically, the control (optical path length control) of a position of the one-axis stage 224 is performed via the optical path length adjustment drive unit 209. After executing the optical path length adjustment processing, the catheter is inserted into the blood vessel, and processing such as an image acquisition in the blood vessel is performed.

In step S506, the control device 103 announces a message prompting the execution of the priming operation (re-operation) to remove air bubbles in the catheter accommodating the imaging core 250. In accordance with an exemplary embodiment, the control device 103 announces a message by any method such as voice output, a text display on the display apparatus 113, an output of a warning sound, and lighting of an LED. Thereafter, the processing returns to S502. This completes a series of processing in FIG. 5. Note that the series of processing in FIG. 5 may be started when the control device 103 detects the execution of the previous priming operation.

Figure 6:
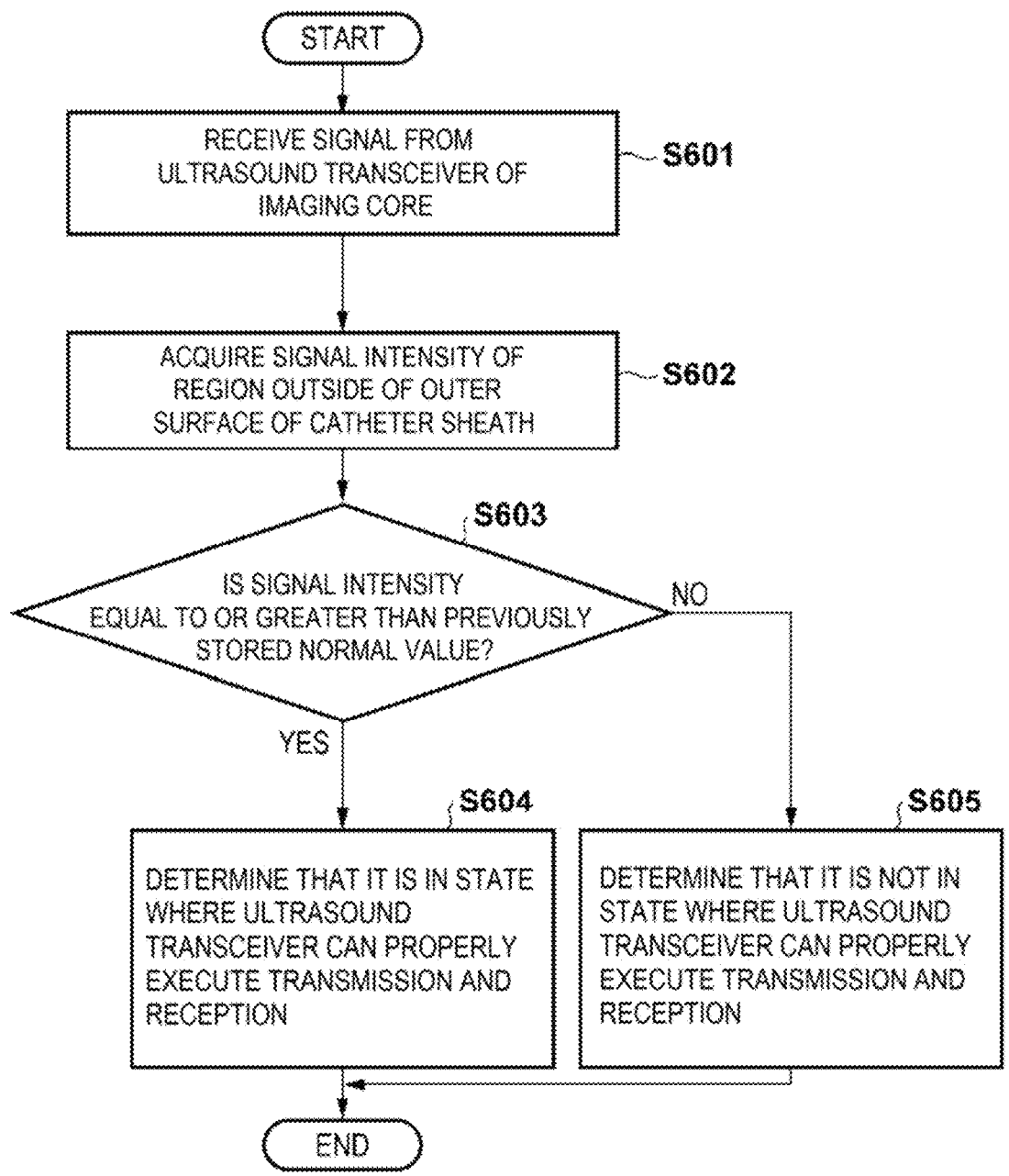
FIG. 6 is a flowchart showing details of processing performed by the control device according to the embodiment of the present disclosure when a signal of an ultrasound receiver is used.
Figure 7:
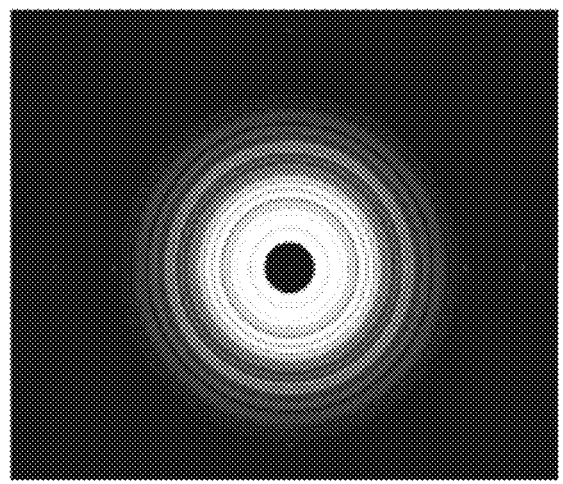
FIG. 7 is a diagram showing an example of an ultrasound tomographic image obtained when no air bubbles are mixed, according to the embodiment of the present disclosure.
Figure 8:
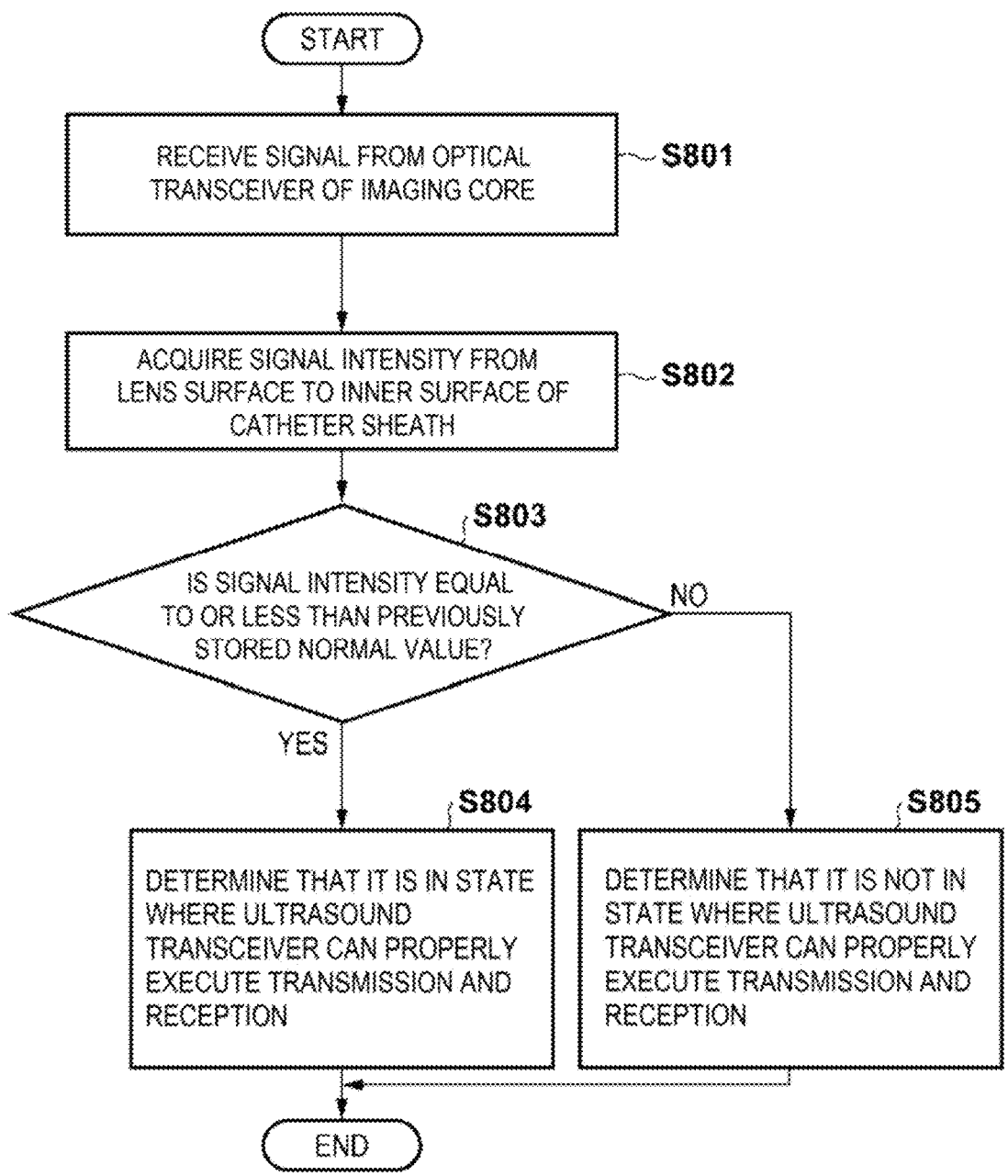
FIG. 8 is a flowchart showing details of processing performed by the control device according to the embodiment of the present disclosure when a signal of an ultrasound receiver is used.

Next, with reference to the flowchart in FIG. 6 and FIG. 7, the details of the processing in S502 and S503 will be described. In this example, it is determined whether or not the imaging core 250 is in a state where the ultrasound transceiver can properly execute the transmission and reception, based on a received signal from the ultrasound transceiver of the imaging core 250. In accordance with this exemplary embodiment, the signal from the optical transceiver is not used.

In step S601, the control device 103 receives a signal from the ultrasound transceiver of the imaging core 250. In step S602, the control device 103 acquires a signal intensity of an outside region of an outer surface of the catheter sheath.

In step S603, the control device 103 determines whether or not the signal intensity acquired in step S602 is equal to or greater than a previously stored threshold value (for example, a predetermined normal value). FIG. 7 shows an example of an ultrasound tomographic image that can be obtained when the priming is correctly performed and air bubbles are not mixed in the catheter accommodating the imaging core 250. If the air bubbles are not mixed in the catheter accommodating the image core 250, as shown in FIG. 7, multiple reflected signals of the catheter sheath are detected, and if the air bubbles are mixed in the catheter accommodating the image core 250, an ultrasound is not transmitted, so that a reflected signal is not obtained and a black image is obtained. If it is determined that the signal intensity is equal to or greater than the previously stored threshold value, the processing proceeds to S604. In accordance with an exemplary embodiment, if it is determined that the signal intensity is less than the previously stored threshold value, the processing proceeds to S605. Alternatively, it may be configured to be determined whether or not a signal received from the ultrasound transceiver includes the reflected signals from the inner surface and the outer surface of the catheter sheath or the multiple reflected signals, and if the reflected signals or the multiple reflected signals are included, it may be determined that the imaging core 250 is in a state where the ultrasound transceiver can properly execute the transmission and reception.

In step S604, the control device 103 determines that the imaging core 250 is in a state where the ultrasound transceiver can properly execute the transmission and reception of signals, and terminates the processing. In step S605, the control device 103 determines that the imaging core 250 is in a state where the ultrasound transceiver can properly execute the transmission and reception of signals, and terminates the processing, which completes a series of processing in FIG. 6.

Next, with reference to the flowchart in FIG. 8 and FIGS. 9A to 9C, the details of the processing in S502 and S503 will be described. In this example, it is determined whether or not the imaging core 250 is in a state wherein the ultrasound transceiver can properly execute the transmission and reception, based on a received signal from the optical transceiver of the imaging core 250. The signal from the ultrasound transceiver is not used in this embodiment.

Figure 9A:
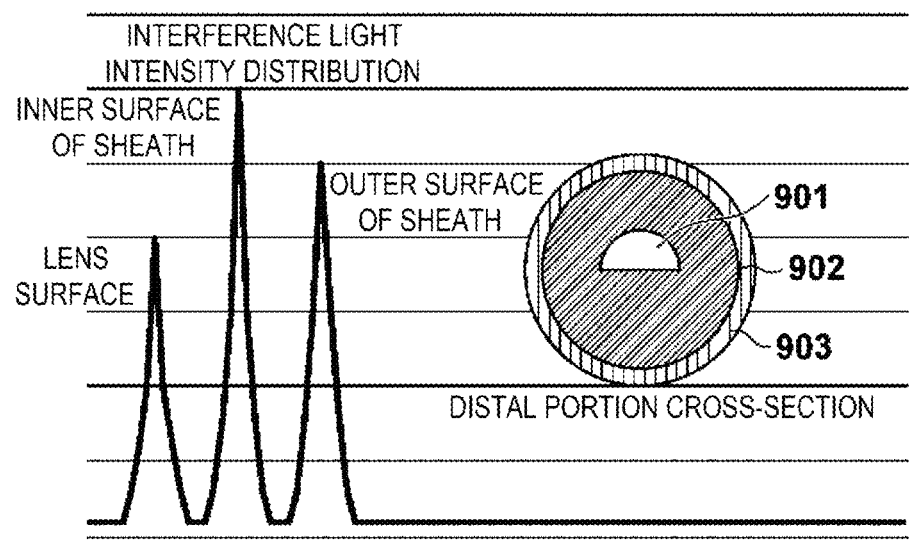
FIGS. 9A, 9B, and 9C are diagrams for explaining an interference light intensity distribution in accordance with presence and absence of mixing of air bubbles according to the embodiment of the present disclosure.
Figure 9B:
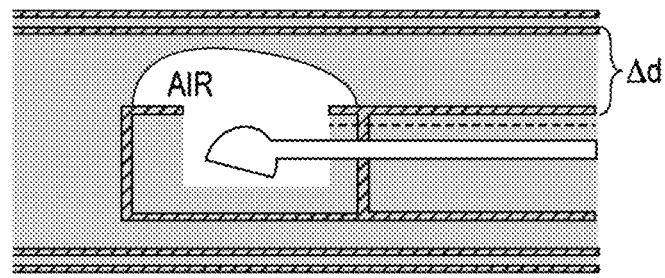
Figure 9C:
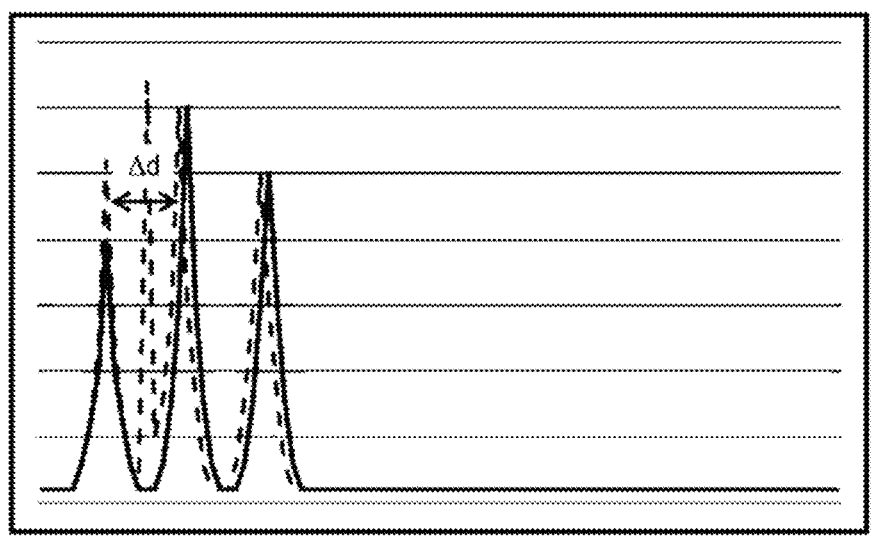

In step S801, the control device 103 receives a signal from the optical transceiver of the imaging core 250. In step S802, the control device 103 acquires a signal intensity of a region from a lens surface constituting a part of the optical transceiver to an inner surface of the catheter sheath. FIGS. 9A to 9C show examples of acquired intensity distribution of interference light. In FIG. 9A, reference numeral 901 denotes the lens surface, 902 denotes the inner surface of the catheter sheath, and 903 denotes the outer surface of the catheter sheath. As shown in FIG. 9A, it can be seen that the intensities of the interference light are increased near the lens surface 901, the catheter sheath inner surface 902, and the catheter sheath outer surface 903. In accordance with an exemplary embodiment, a normal value (or signal intensity) in a situation without mixed air bubbles (i.e., no air bubbles) is distributed as shown in FIG. 9A.

In step S803, the control device 103 determines whether or not the signal intensity acquired in step S802 is equal to or less than the previously stored threshold value. FIG. 9B shows a vertical cross-sectional diagram of a distal portion of the imaging core 250 when air bubbles (air) are mixed. When the air bubbles are mixed as described above, as indicated by a broken line in FIG. 9C, the value becomes larger in a range of Δd than the normal value in FIG. 9A (that is, the region from the lens surface to the inner surface of the catheter sheath). The fact that the signal intensity acquired in S802 is equal to or less than the previously stored threshold value can be considered to indicate a state where the ultrasound transceiver can properly execute the transmission and reception of signals (a state where no air bubbles are present). A solid line in FIG. 9C shows the same as the interference light intensity distribution in FIG. 9A.

In the processing in S803, the control device 103 may be configured to compare an integrated value of the signal intensity in the range of Δd with an integrated value of the normal value in the same range, or to compare average values in the range of Δd with each other. In addition, the control device 103 may be configured to compare signal intensities at specific coordinates within the range of Δd with each other. At that time, in order to reduce the influence of error, it may be determined that the air bubbles are mixed when the difference between the two compared values is equal to or greater than the threshold value.

In accordance with an exemplary embodiment, if it is determined that the signal intensity is equal to or less than the previously stored threshold value, the processing proceeds to S804. Alternatively, if it is determined that the signal intensity is greater than the previously stored threshold value, the processing proceeds to S805.

In step S804, the control device 103 determines that the imaging core 250 is in a state where the ultrasound transceiver can properly execute the transmission and reception of signals, and terminates the processing. In step S805, the control device 103 determines that the image core 250 is in a state wherein the ultrasound transceiver can properly execute the transmission and reception of signals, and terminates the processing, which completes a series of processing in FIG. 8.

As described above, referring to FIGS. 6 to 9C, there have been described examples, in which whether or not it is in a state where the ultrasound transceiver can properly execute the transmission and reception of signals is determined based on the signal of the ultrasound transceiver or determined based on the signal of the optical transceiver. The present disclosure is not limited to these examples, and it may be determined by using the signals of both of these transceivers. Specifically, the processes in FIGS. 6 and 8 may each be executed, and when it is determined in both processes that the imaging core 250 is in a state where the ultrasound transceiver can properly execute the transmission and reception of signals, it may be determined that the imaging core 250 is in a state where the ultrasound transceiver can properly execute the transmission and reception of signals in S503. In addition, it may be determined whether or not the imaging core 250 is in a state where the ultrasound transceiver can properly execute the transmission and reception, based on an intensity of the received signal or a signal interval from the inner surface of the catheter sheath or the inside region of the inner surface of the catheter sheath which are received from the optical transceiver.

As described above, a control device 103 according to the present embodiment receives signals from an imaging core including an optical transceiver and an ultrasound transceiver, determines whether or not the imaging core 250 is in a state where the ultrasound transceiver can properly execute transmission and reception, based on at least one of the signal from the optical transceiver and the signal from the ultrasound transceiver which are received by the receiving unit, and controls execution of an optical path length adjustment for imaging with the optical transceiver when it is determined that the ultrasound transceiver can properly execute the transmission and reception.

In accordance with an exemplary embodiment, it is possible to automatically execute a series of operations such as a confirmation operation of whether or not air bubbles remain before acquiring the IVUS image, and an optical path length adjustment operation necessary before acquiring the OCT image. In accordance with an exemplary embodiment, it is necessary to perform the optical path length adjustment after the priming is performed and it is confirmed that no air bubble is mixed. However, according to the processing of the present disclosure, a user can be prevented from performing an erroneous procedure and help prevent an occurrence of an erroneous diagnosis. In this way, it is possible to reduce a burden of prior confirmation by a user, and to prevent an occurrence of an erroneous diagnosis.

Although a dual sensor having the IVUS function and the OCT function has been described in the present embodiment, it may not be always necessary to operate both functions at the time of diagnosis, and there may be a case where it is desired to operate only one function.

In accordance with an exemplary embodiment, the control device 103 may be configured to receive a mode selection in accordance with a user operation from among a first mode in which imaging using the optical transceiver is executed, a second mode in which imaging using the ultrasound transceiver is executed, and a third mode in which imaging using the optical transceiver and imaging using the ultrasound transceiver are executed. Further, when the second mode is selected, the optical path length adjustment may not be executed, which helps make it possible to reduce the time required for unnecessary processing.

In accordance with an exemplary embodiment, with reference to FIG. 10, description will be given of turned-back of signals according to the embodiment of the present disclosure. In OCT, turned-back of a signal may occur by performing Fourier transformation. Since a positional relationship of each signal on the lens surface, on the inner surface of the catheter sheath, and on the outer surface of the catheter sheath changes when a turned-back signal is generated, it is necessary to determine whether or not the image core 250 is in a state where there is no turned-back signal. In a state where the optical path length adjustment is not performed, the three signals obtained from the lens surface, the inner surface of the catheter sheath and the outer surface of the catheter sheath, have various positional relationships due to variations in the fiber length of the catheter.

Figure 10:
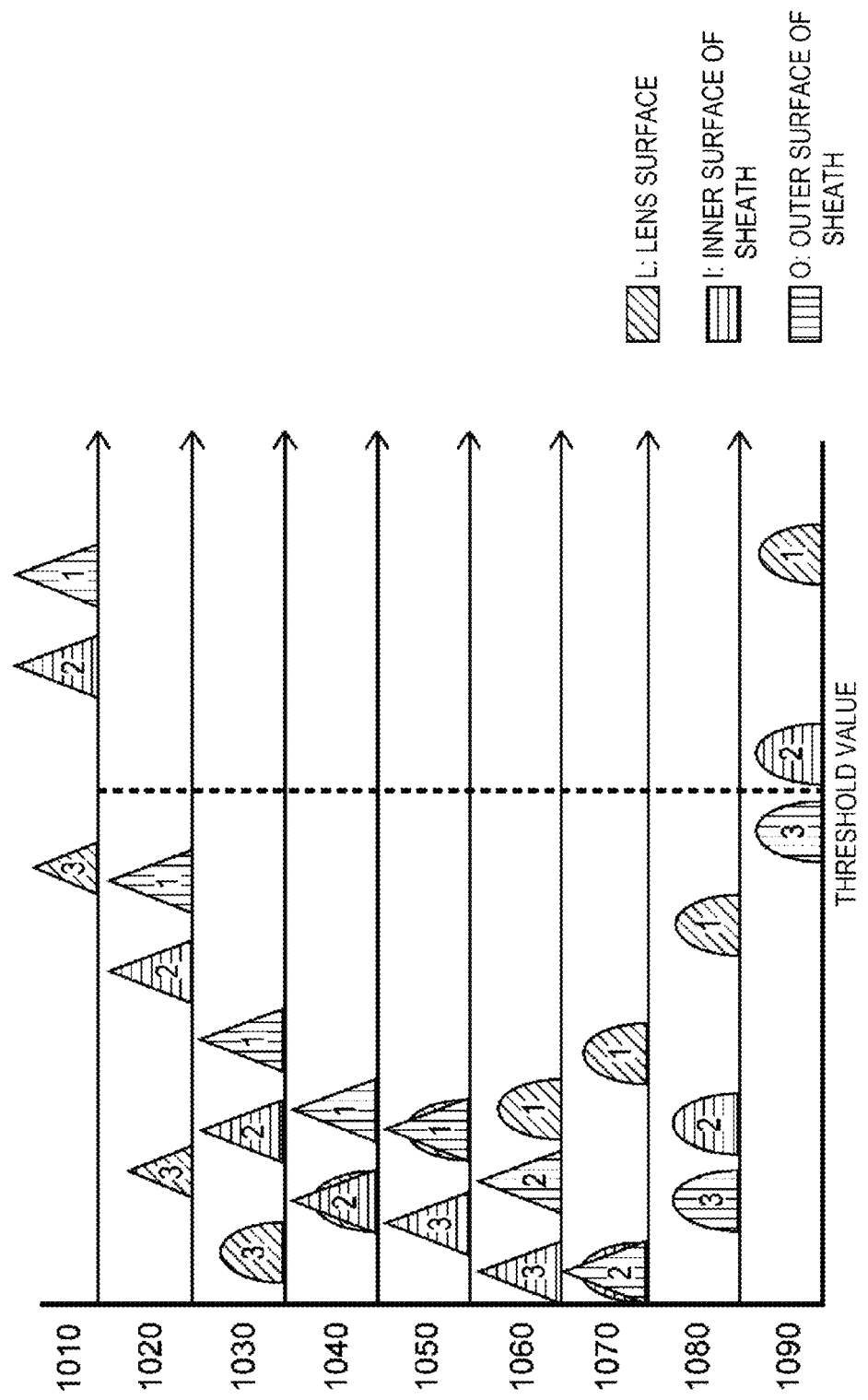
FIG. 10 is a diagram for explaining a turned-back of signals according to an embodiment of the present disclosure.

In FIG. 10, a horizontal axis represents an optical path difference, and for each reflected signal from the lens surface, the inner surface of the catheter sheath, and the outer surface of the catheter sheath, numbers are assigned as a first signal, a second signal, and a third signal in order from a signal having a larger optical path difference. When each waveform of a state 1010 shifts to a left side, a state 1020 is obtained, and in the state 1010 and the state 1020, no turned-back of a signal has occurred.

When each waveform of the state 1020 shifts to the left side, the state 1030 is obtained, and a waveform of the lens surface is turned back with using an origin as a boundary. In order to distinguish the waveform of the lens surface which is turned back from the waveforms of the inner surface of the catheter sheath and outer surface of the catheter sheath (shown in a triangle) which are not turned back, the waveform of the lens surface which is turned back is shown in a parabolic form. As a state 1040 transitions to a state 1090, the waveforms of the inner surface of the catheter sheath and the outer surface of the catheter sheath are also turned back with using the origin as a boundary.

Determination processing should be performed in the absence of such turned-back to determine whether or not the imaging core 250 is in a state where the ultrasound transceiver can properly execute the transmission and reception of signals. An interval between a signal on the inner surface of the catheter sheath and a signal on the outer surface of the catheter sheath is always constant. In addition, when the three signals obtained from the lens surface, the inner surface of the catheter sheath and the outer surface of the catheter sheath are turned back, the signal on the lens surface occurs on the side where the optical path difference is large.

When the signal on the inner surface of the catheter sheath and the signal on the outer surface of the catheter sheath are each positioned at a position larger than a certain optical path difference (threshold value), it is determined that the imaging core 250 is in a state where there is no turned-back signal. In an example of FIG. 10, it is determined that the state 1010 is such that there is no turned-back signal and other states 1020 to 1090 are such that there are turned-back signals.

The turned-back of a signal is not actually occurred in the state 1020. However, in order to clearly distinguish between the state 1020 and the state 1030, it is conditional that the signal on the inner surface of the catheter sheath and the signal on the outer surface of the catheter sheath are each positioned at a position greater than a certain optical path difference (threshold value). As a result, it is determined that only the state 1010 is such that there is no turned-back signal.

As described above, before executing the determination processing as to whether or not the imaging core 250 is in a state where the ultrasound transceiver can properly execute the transmission and reception of signals, if reflected signals obtained from the optical transceiver are set to be a first signal and a second signal in order from a signal having a larger optical path difference, it can be determined that the image core 250 is in a state where turned-back does not occur (state 1010) when an interval between the first signal and the second signal is a predetermined value, and an optical path difference of the first signal and the optical path difference of the second signal are equal to or greater than a threshold value respectively. Therefore, in this case, the control device 103 can be is configured so as to execute the determination processing.

Figure 11:
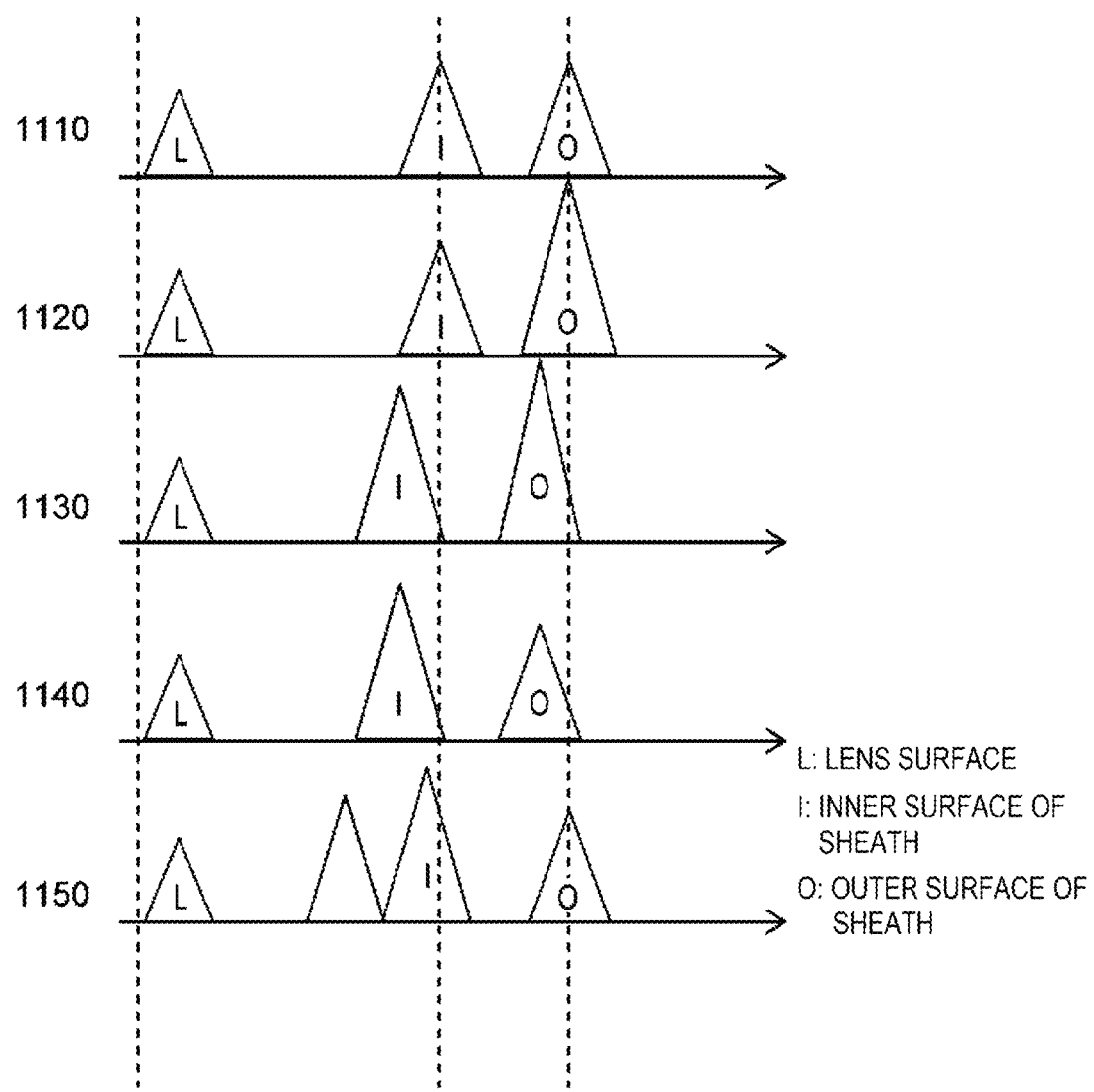
FIG. 11 is a diagram for explaining a relationship between a signal interval and signal intensity, and a state of the ultrasound receiver according to the embodiment of the present disclosure.

Next, with reference to FIG. 11, a relationship between a signal interval and a signal intensity, and a state of the ultrasound receiver according to the embodiment of the present disclosure will be described. In FIG. 11, a horizontal axis represents an optical path difference and a vertical axis represents signal intensity. In addition, a triangle with a letter L represents a waveform of the lens surface, a triangle with a letter I represents a waveform of the inner surface of the catheter sheath, and a triangle with a letter O represents a waveform of the outer surface of the catheter sheath.

A state 1110 is a case where a region inside the catheter is water (saline solution) and a region outside the catheter is also water. The region inside the catheter is filled with water, and the imaging core 250 is in a proper priming state, that is, a state where the ultrasound transceiver can properly execute the transmission and reception of signals. A state 1120 is a case where a region inside the catheter is water and a region outside the catheter is air. The region inside the catheter is filled with water, and the imaging core 250 is in a proper priming state, that is, a state where the ultrasound transceiver can properly execute the transmission and reception of signals. Note that a signal intensity of the outer surface of the catheter sheath in which air exists becomes high.

A state 1130 is a case where a region inside the catheter is air and a region outside the catheter is also air. Inside the catheter is filled with air, and the imaging core 250 is not in a proper priming state, that is, the imaging core 250 is not in a state where the ultrasound transceiver can properly execute the transmission and reception of signals. Note that a signal intensity of the outer surface of the catheter sheath and a signal intensity of the inner surface of the catheter sheath, in which air exists, become high. In addition, an interval between the signal of the lens surface and the signal of the inner surface of the catheter sheath becomes relatively small.

A state 1140 is a case where a region inside the catheter is air and a region outside the catheter is water. Inside the catheter is filled with air, and the imaging core 250 is not in a proper priming state, that is, the imaging core 250 is not in a state where the ultrasound transceiver can properly execute the transmission and reception of signals. Note that a signal intensity of the inner surface of the catheter sheath in which air exists becomes relatively high. In addition, an interval between the signal of the lens surface and the signal of the inner surface of the catheter sheath becomes relatively small.

A state 1150 is a case where a region inside the catheter is air and water (that is, a part of the inside the catheter is water), and a region outside the catheter is water. Air is included in the region inside the catheter, and the imaging core 250 is not in a proper priming state, that is, the imaging core 250 is not in a state where the ultrasound transceiver can properly execute the transmission and reception of signals. Note that another signal is detected between the signal of the lens surface and the signal of the inner surface of the catheter sheath.

Therefore, when an interval between the reflected signal from the lens surface received from the optical transceiver and the reflected signal from the inner surface of the catheter sheath is equal to or greater than the threshold value (state 1110 and state 1120), it is possible to determine that the imaging core 250 is in a state where the ultrasound transceiver can properly execute the transmission and reception. Further, when an intensity of a reflected signal from the inner surface of the catheter sheath received from the optical transceiver is equal to or less than the threshold value (state 1110 and state 1120), it is possible to determine that the imaging core 250 is in a state where the ultrasound transceiver can properly execute the transmission and reception. In accordance with an exemplary embodiment, when a signal received within a region from the lens surface to the inner surface of the catheter sheath is a reflected signal where an intensity of the signal is equal to or greater than a threshold value (state 1150), it is possible to determine that the imaging core 250 is in a state where the ultrasound transceiver can properly execute the transmission and reception.

The present disclosure is not limited to the above embodiment, and various modifications and variations are possible without departing from the spirit and scope of the present disclosure. Accordingly, in order to publicize the scope of the present disclosure, the following claims are attached.

The detailed description above describes to a control device, an image diagnosis apparatus, a method for processing of a control device, and a program. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A control device comprising:
a processor configured to:
   detect a connection of a catheter accommodating an imaging core to the control device, the imaging core including an optical transceiver and an ultrasound transceiver;
   receive a signal from the imaging core;
   determine whether the imaging core is in a state where the ultrasound transceiver is able to properly execute transmission and reception, based on at least one of a signal from the optical transceiver and a signal from the ultrasound transceiver, from the signal received from the imaging core;
   control a movement of the imaging core with a pullback unit to a distal side of the catheter after the determination that the ultrasound transceiver is able to properly execute the transmission and reception and before an execution of an optical path adjustment with an optical path length adjustment unit; and control the execution of the optical path length adjustment for imaging with the optical transceiver after the movement of the imaging core to the distal side of the catheter and the determination that the ultrasound transceiver is able to properly execute transmission and reception and before performing an initial image acquisition in a blood vessel with the imaging core.

2. The control device according to claim 1, wherein the processor determines that the imaging core is in a state where the ultrasound transceiver is able to properly execute the transmission and reception when the signals received from the ultrasound transceiver include a reflected signal or multiple reflected signals from an inner surface and an outer surface of a catheter sheath of the catheter.

3. The control device according to claim 1, wherein the processor determines that the imaging core is in a state where the ultrasound transceiver is able to properly execute transmission and reception based on an intensity or a signal interval of received signals from an inner surface of a catheter sheath of the catheter or a region inside of the inner surface of the catheter sheath of the catheter, which are received from the optical transceiver.

4. The control device according to claim 1, wherein, before determining if the imaging core is the state wherein the ultrasound transceiver is able to properly execute the transmission and reception, when reflected signals obtained from the optical transceiver are set to be a first signal and a second signal in order from a signal having a larger optical path difference, and wherein the processor is configured to execute the determination of whether the imaging core is in the state wherein the ultrasound transceiver is able to properly execute the transmission and reception when an interval between the first signal and the second signal is a predetermined value, and an optical path difference of the first signal and an optical path difference of the second signal are equal to or greater than a threshold value, respectively.

5. The control device according to claim 3, wherein when an interval, between a reflected signal from a lens surface and a reflected signal from the inner surface of the catheter sheath of the catheter, which are received from the optical transceiver, is equal to or greater than a threshold value, the processor determines that the imaging core is in a state where the ultrasound transceiver is able to properly execute the transmission and reception.

6. The control device according to claim 3, wherein when an intensity of a reflected signal from the inner surface of the catheter sheath of the catheter, which is received from the optical transceiver is equal to or less than a threshold value, the processor determines that the imaging core is in a state where the ultrasound transceiver is able to properly execute the transmission and reception.

7. The control device according to claim 3, wherein when a signal received within a region from a lens surface to the inner surface of the catheter sheath of the catheter is a reflected signal where an intensity of the signal is equal to or greater than a threshold value, the processor determines that the imaging core is not in a state where the ultrasound transceiver is able to properly execute the transmission and reception.

8. The control device according to claim 1, wherein the state where the ultrasound transceiver is able to properly execute the transmission and reception is when air bubbles are not present in the catheter accommodating the imaging core.

9. The control device according to claim 1, wherein the processor is configured to:

send a message prompting execution of a priming operation for removing the air bubbles in the catheter accommodating the imaging core when the processor determines that the ultrasound transceiver is not able to properly execute the transmission and reception.

10. The control device according to claim 1, wherein the processor is configured to:

select a mode, based on a user operation, from among a first mode in which imaging using the optical transceiver is executed, a second mode in which imaging using the ultrasound transceiver is executed, and a third mode in which imaging using the optical transceiver and imaging using the ultrasound transceiver are executed; and when the second mode is selected, the optical path length adjustment is not executed.

11. An image diagnosis apparatus, comprising:

the control device according to claim 1; and the catheter configured to accommodate the imaging core, the catheter including the optical transceiver and the ultrasound transceiver, the pull-back unit, and the optical path length adjustment unit.

12. A non-transitory computer readable medium containing a computer program having computer readable code embodied to carry out a process of a control device, the process comprising:

detecting a connection of a catheter accommodating an imaging core to the control device, the imaging core including an optical transceiver and an ultrasound transceiver;

receiving a signal from the imaging core;

determining whether the control device is in a state where the ultrasound transceiver is able to properly execute transmission and reception, based on at least one of a signal from the optical transceiver and a signal from the ultrasound transceiver which are received from the signal from the imaging core;

controlling a movement of the imaging core to a distal side of the catheter after the determination that the ultrasound transceiver is able to properly execute the transmission and reception and before an execution of an optical path adjustment with an optical path length adjustment unit; and controlling the execution of the optical path length adjustment for imaging with the optical transceiver after the movement of the imaging core to the distal side of the catheter and the determination that the ultrasound transceiver is able to properly execute the transmission and reception and before performing an initial image acquisition in a blood vessel with the imaging core.

13. A method for processing of a control device, comprising:

detecting a connection of a catheter accommodating an imaging core to the control device, the imaging core including an optical transceiver and an ultrasound transceiver;

receiving a signal from an imaging core;

determining whether the control device is in a state where the ultrasound transceiver is able to properly execute transmission and reception, based on at least one of a signal from the optical transceiver and a signal from the ultrasound transceiver which are received from the signal from the imaging core;

controlling a movement of the imaging core to a distal side of the catheter after the determination that the ultrasound transceiver is able to properly execute the transmission and reception and before an execution of an optical path adjustment with an optical path length adjustment unit; and controlling the execution of the optical path length adjustment for imaging with the optical transceiver after the movement of the imaging core to the distal side of the catheter and the determination that the ultrasound transceiver is able to properly execute the transmission and reception and before performing an initial image acquisition in a blood vessel with the imaging core.

14. The method according to claim 13, further comprising:

determining that the imaging core is in a state where the ultrasound transceiver is able to properly execute the transmission and reception when the signals received from the ultrasound transceiver include a reflected signal or multiple reflected signals from an inner surface and an outer surface of a catheter sheath of the catheter.

15. The method according to claim 13, wherein further comprising:

determining whether the imaging core is in a state where the ultrasound transceiver is able to properly execute the transmission and reception based on an intensity or a signal interval of received signals from an inner surface of a catheter sheath of the catheter or a region inside of the inner surface of the catheter sheath of the catheter, which are received from the optical transceiver.

16. The method according to claim 13, wherein, before determining if the imaging core is the state wherein the ultrasound transceiver is able to properly execute the transmission and reception, when reflected signals obtained from the optical transceiver are set to be a first signal and a second signal in order from a signal having a larger optical path difference, the method comprising:

executing the determination of whether the imaging core is the state wherein the ultrasound transceiver is able to properly execute the transmission and reception, when an interval between the first signal and the second signal is a predetermined value, and an optical path difference of the first signal and an optical path difference of the second signal are equal to or greater than a threshold value, respectively.

17. The method according to claim 15, wherein, when an interval, between a reflected signal from a lens surface and a reflected signal from the inner surface of the catheter sheath, which are received from the optical transceiver, is equal to or greater than a threshold value, or wherein when an intensity of a reflected signal from the inner surface of the catheter sheath, which is received from the optical transceiver is equal to or less than a threshold value, determining that the imaging core is in a state where the ultrasound transceiver is able to properly execute the transmission and reception; and when a signal received within a region from a lens surface to the inner surface of the catheter sheath is a reflected signal where an intensity of the signal is equal to or greater than a threshold value, determining that the imaging core is not in a state where the ultrasound transceiver is able to properly execute the transmission and reception.

18. The method according to claim 13, wherein after the execution of the optical path length adjustment, the method comprising:

inserting the catheter into the blood vessel; and performing the image acquisition in the blood vessel with the imaging core.

* * * * *